United States Patent
Ollivier et al.

(10) Patent No.: US 8,399,716 B2
(45) Date of Patent: Mar. 19, 2013

(54) METHOD OF PURIFYING ALCOHOL FROM A FERMENTATION BROTH

(75) Inventors: Frederic Ollivier, Lyons (FR); Pascal Rousseaux, Lyons (FR)

(73) Assignee: Metabolic Explorer, Saint Beauzire (FR)

( * ) Notice: Subject to any disclaimer, the term of this patent is extended or adjusted under 35 U.S.C. 154(b) by 393 days.

(21) Appl. No.: 12/743,988

(22) PCT Filed: Nov. 30, 2007

(86) PCT No.: PCT/EP2007/063068
§ 371 (c)(1),
(2), (4) Date: May 20, 2010

(87) PCT Pub. No.: WO2009/068110
PCT Pub. Date: Jun. 4, 2009

(65) Prior Publication Data
US 2010/0261240 A1    Oct. 14, 2010

(51) Int. Cl.
*C07C 27/26* (2006.01)

(52) U.S. Cl. ........ 568/868; 210/806; 210/314; 210/639; 435/158

(58) Field of Classification Search .................. 568/868; 435/581; 210/314, 639, 806
See application file for complete search history.

(56) References Cited

U.S. PATENT DOCUMENTS

| 4,584,063 | A | 4/1986 | Berg et al. |
| 6,361,983 | B1 | 3/2002 | Ames |
| 6,603,048 | B1 * | 8/2003 | Corbin et al. ................. 568/868 |
| 7,919,658 | B2 * | 4/2011 | Adkesson et al. ............ 568/868 |
| 2004/0222153 | A1 | 11/2004 | Baniel et al. |

FOREIGN PATENT DOCUMENTS

| EP | 1 218 327 | 7/2002 |
| WO | 2004/101479 | 11/2004 |
| WO | 2006/025697 | 3/2006 |

OTHER PUBLICATIONS

Gong et al.; "The Possibility of the Desalination of Actual 1,3-Propanediol Fermentation Broth by Electrodialysis"; Desalination; 161 (2004) pp. 169-178.
Gong et al.; "Effects of Transport Properties of Ion-Exchange Membranes on Desalination of 1,3-Propanediol Fermentation Broth by Electrodialysis"; Desalination; 191 (2006) pp. 193-199.
International Search Report based on PCT/EP2007/063068 dated Sep. 19, 2008.
Gonzalez-Pajuelo et al.; "Metabolic Engineering of Clostridium Acetobutylicum for the Industrial Production of 1, 3-Propanediol From Glycerol"; Metabolic Engineering, Academic Press, US, vol. 7, No. 5-6, Sep. 1, 2005, pp. 329-336.

* cited by examiner

*Primary Examiner* — Robert A Hopkins
(74) *Attorney, Agent, or Firm* — Baker Donelson Bearman Caldwell & Berkowitz, PC

(57) ABSTRACT

Method for purifying an alcohol, notably 1,3-propanediol, from a fermentation broth.

10 Claims, 7 Drawing Sheets

METHOD OF PURIFYING ALCOHOL FROM A FERMENTATION BROTH

CROSS REFERENCE TO RELATED APPLICATIONS

Figure 1:
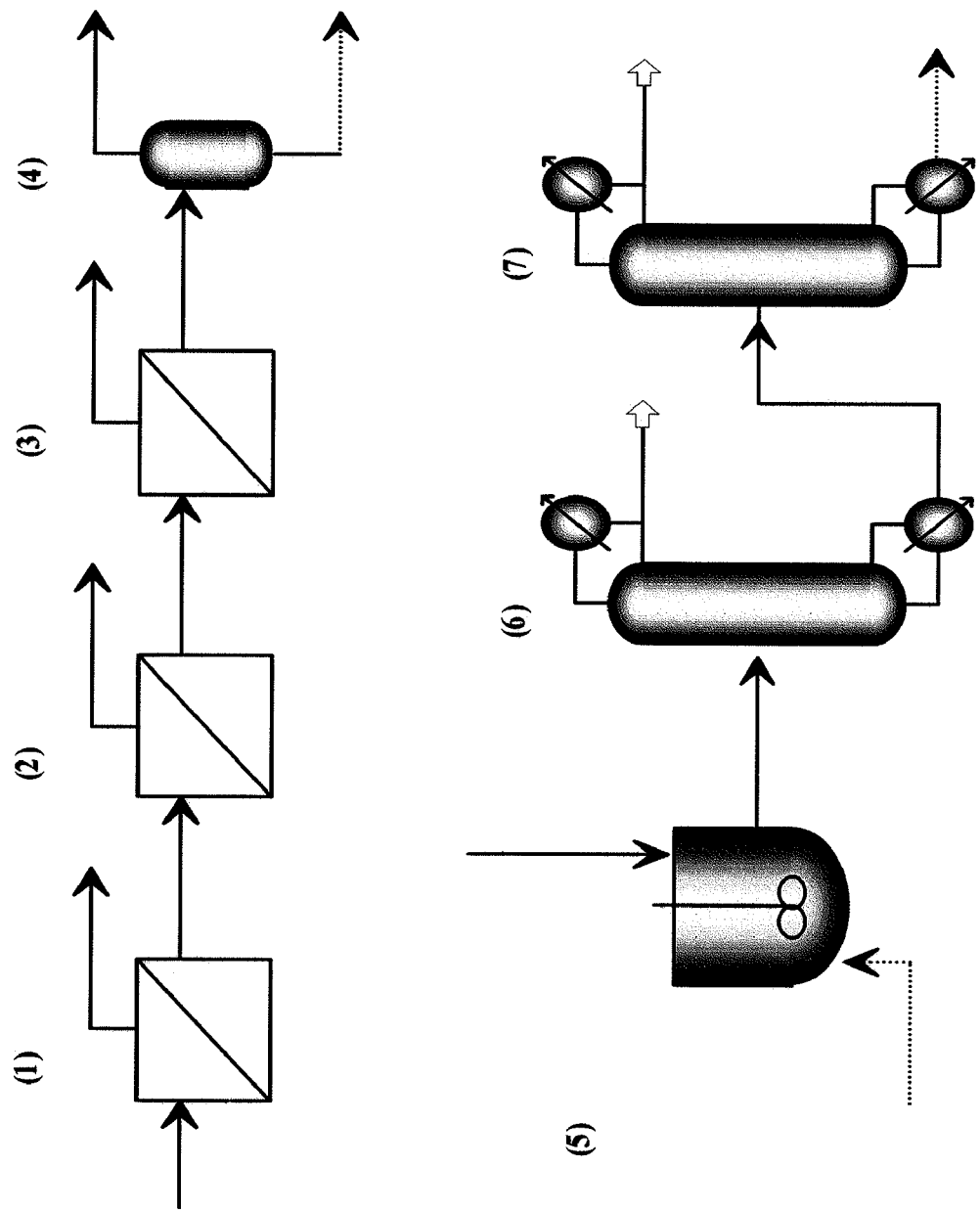

This application is a §371 National Stage Application of PCT/EP2007/063068 filed Nov. 30, 2007.

BACKGROUND OF THE INVENTION

1. Field of the Invention

The present invention relates to the purification of an alcohol from a fermentation broth.

2. Description of Related Art

The production of alcohol by microbial fermentation has many advantages. For example, the production of butanol, 1,3-propanediol and 1,2-propanediol by fermentation are well known. The raw material in the fermentation medium can be glycerol. The synthesis of 1,3-propanediol by fermentation of glycerol by clostridium has been described in particular. The synthesis of 1,3-propanediol by fermentation of glycerol provides a significant reduction in production costs compared to chemical synthesis using petroleum products.

The production of alcohols by fermentation is often accompanied by the production of organic acids and/or ketones. Thus, the production of 1,3-propanediol by microbial fermentation can be accompanied by the co-production of other products including acetone or acids in the form acetic and/or butyric acids or acetate and/or butyrate salt.

The alcohol produced by fermentation must then be purified from the fermentation broth. The fermentation broth can contain by-products that are also advantageous to purify (acetone, butyrate or acetate, for example) in addition to, typically, water, organic impurities, mineral salts and organic salts.

In the specific case of 1,3-propanediol, organic impurities responsible for 1,3-propanediol's color and odor are often observed. These impurities have not been identified but it is possible that they occur due to 1,3-propanediol degradation. Such degradation must thus be avoided during 1,3-propanediol production and purification.

A problem encountered during the purification of alcohol from fermentation broth is the elimination of salts. These salts are typically sodium chlorides and calcium chlorides but also ammonium and phosphate salts. The concentration of these salts in the fermentation broth controls their precipitation during alcohol purification.

Many methods for purifying 1,3-propanediol from fermentation broth have been described, notably EP 1,218,327, U.S. Pat. No. 7,056,439, EP 1,103,618 and WO2004/101479.

With regard to salts, most notably it has been proposed to eliminate salts upstream from the purification method by various techniques such as the use of ion-exchange resins (WO2004101479), electrodialysis (Gong et a)., 2006; Gong et al., 2004) and precipitation-filtration (U.S. Pat. No. 6,361,983).

However, these techniques do not always provide satisfactory results.

The present invention proposes a novel method for purifying an alcohol, notably 1,3-propanediol, from a fermentation broth.

Advantageously, the methods according to the present invention avoid the precipitation of salts during the purification of alcohol from the fermentation broth. In the inventive methods, the addition of glycerol solubilizes salts in order to retain them in the liquid phase until the end of the purification process.

Advantageously, the methods according to the present invention prevent the appearance of the impurities responsible for 1,3-propanediol color and odor.

According to another advantage of the present invention, the methods of the present invention provide improved yield.

DESCRIPTION OF THE INVENTION

The invention relates to methods for purifying an alcohol from a fermentation broth comprising at least the following steps:
- filtering the fermentation broth in order to obtain an aqueous solution containing the alcohol,
- adding glycerol to the aqueous solution,
- recovering the alcohol.

In one embodiment of the invention, the purification method comprises at east the following steps:
- filtering the fermentation broth in order to obtain an aqueous solution containing the alcohol,
- eliminating water from the aqueous solution,
- adding glycerol to the aqueous solution,
- recovering the alcohol.

In one embodiment of the invention, the purification method comprises at least the following steps:
- filtering the fermentation broth in order to obtain an aqueous solution containing the alcohol,
- eliminating water from the aqueous solution,
- adding glycerol to the aqueous solution,
- eliminating by distillation products with a vapor pressure greater than that of the alcohol to be purified,
- eliminating by distillation products with a vapor pressure less than that of the alcohol to be purified.
- recovering the alcohol.

In a specific embodiment of the invention, the purification method also comprises a step of adjusting the pH of the aqueous solution to pH<7.

In another specific embodiment of the invention, the purification method also comprises a step of extracting with a hydrophobic solvent to eliminate organic acids.

In another embodiment of the invention, the purification method also comprises a step of eliminating anions in the aqueous solution.

Preferably, water is eliminated by evaporation in the inventive methods.

Preferentially, glycerol is added in proportions ranging from 5% to 100% by weight of the aqueous solution.

The invention thus relates to the use of glycerol to purify an alcohol from a fermentation broth.

In a preferred embodiment of the invention, the alcohol to be purified from the culture broth is 1,3-propanediol.

Advantageously, after recovering the alcohol, glycerol is recovered.

Glycerol may be recovered by standard methods well known to the skilled person. Glycerol may for example be recovered by distillation.

According to a first embodiment, the method for purifying an alcohol from a culture broth comprises at least the following steps:
- filtering the fermentation broth in order to obtain an aqueous solution containing the alcohol,
- evaporating water in the aqueous solution,
- adding glycerol to the aqueous solution,
- eliminating by distillation products with a vapor pressure greater than that of the alcohol to be purified, eliminating by distillation products with a vapor pressure less than that of the alcohol to be purified,
recovering the alcohol.

In another embodiment of the invention, the purification method comprises at least the following steps:
filtering the fermentation broth in order to obtain an aqueous solution containing the alcohol,
evaporating water in the aqueous solution.
adjusting the pH of the aqueous solution to pH<7, preferably <3,
adding glycerol to the aqueous solution,
eliminating by distillation products with a vapor pressure greater than that of the alcohol to be purified,
eliminating by distillation products with a vapor pressure less than that of the alcohol to be purified,
recovering the alcohol.

In another embodiment of the invention, the purification method comprises at least the following steps:
filtering the fermentation broth in order to obtain an aqueous solution containing the alcohol,
evaporating water in the aqueous solution,
adjusting the pH of the aqueous solution to pH<7, preferably <3,
extracting with a hydrophobic solvent to eliminate organic acids,
adding glycerol to the aqueous solution,
eliminating by distillation products with a vapor pressure eater than that of the alcohol to be purified,
eliminating by distillation products with a vapor pressure less than that of the alcohol to be purified,
recovering the alcohol.

In another embodiment of the invention, the purification method comprises at east the following steps:
filtering the fermentation broth in order to obtain an aqueous solution containing the alcohol.
eliminating anions in the aqueous solution, preferably by a strong ion-exchange resin,
evaporating water in the aqueous solution,
adding glycerol to the aqueous solution,
eliminating by distillation products with a vapor pressure greater than that of the alcohol to be purified,
eliminating by distillation products with a vapor pressure less than that of the alcohol to be purified,
recovering the alcohol.

In another embodiment of the invention, the purification method comprises at least the following steps:
quenching fermentation by adding a base
filtering the fermentation broth in order to obtain an aqueous solution containing the alcohol,
evaporating water in the aqueous solution,
adding glycerol to the aqueous solution,
eliminating by distillation products with a vapor pressure greater than that of the alcohol to be purified,
eliminating by distillation products with a vapor pressure less than that of the alcohol to be purified,
recovering the alcohol.

In another embodiment of the invention, the purification method comprises at least the following steps:
filtering the fermentation broth in order to obtain an aqueous solution containing the alcohol,
evaporating water in the aqueous solution,
adding glycerol to the aqueous solution,
bleaching,
eliminating by distillation products with a vapor pressure greater than that of the alcohol to be purified,
eliminating by distillation products with a vapor pressure less than that of the alcohol to be purified,
recovering the alcohol.

The invention thus relates to the purification of an alcohol from a fermentation broth. "Alcohol" means a molecule with at least one alcohol function. Preferably, the alcohol to be purified is a diol or a heavy alcohol. Preferentially, the alcohol is selected from among butanol, 1,3-propanediol and 1,2-propanediol. More preferentially, the invention relates to the purification of 1,3-propanediol from a fermentation broth.

Advantageously, the raw material used in the production of alcohol by fermentation is glycerol.

Thus, the invention most notably relates to the purification of 1,3-propanediol from a fermentation broth. 1,3-propanediol can, for example, be produced by the fermentation of glycerol. Such fermentation leads to the co-production of sodium and ammonium butyrate or acetate and/or acetone. The fermentation broth obtained after fermentation contains, for example, water, 1,3-propanediol, glycerol, butyrate and acetate mineral salts and organic salts. The noble products to recover are 1,3-propanediol and acetone (or acids in the form of acetic and/or butyric acid or acetate and/or butyrate salts). Acetone can be recovered according to known techniques such as, for example, by stripping the solution with carbon dioxide.

In the methods according to the present invention, the fermentation reaction can optionally be quenched by adding a base to the fermentation broth. A base is added, for example, in the form of soda, potash or ammonia with the purpose of arresting bacterial activity. The pH achieved is between 7.5 and 14.

Next, the first step of the alcohol purification method consists of filtering the fermentation broth to eliminate insoluble elements, most notably large molecules, biomass, proteins and all suspended particles. Preferably, all molecules heavier than 200 Da are eliminated. "Filtering" preferentially means a membrane separation method. Advantageously, filtration consists successively of microfiltration, ultrafiltration and nanofiltration.

The purification method also comprises a step of adding glycerol to the aqueous solution. The added glycerol helps solubilize the salts present in the solution. Preferably, glycerol is added in proportions ranging from 5%, 10%, 20%, 30%, 40%, 50%, 60%, 70%, 80%, 90% to 100% by weight of the aqueous solution. Glycerol, in particular biodiesel-based glycerol, can contain sodium chloride as well as other anions. Thus it may be advantageous to pre-treat the glycerol beforehand, with a strong anion-exchange resin, for example, in order to eliminate anions.

After adding glycerol to the aqueous solution, the alcohol is then purified and recovered. The alcohol can be purified according to any known alcohol-purification technique, in particular by distillation. Advantageously, topping and stripping are performed.

Optionally, the method according to the present invention also comprises a step of eliminating water and thus of concentrating the aqueous solution. Water can be eliminated by various techniques known to persons skilled in the art. In a preferred embodiment of the purification method according to the invention, water is eliminated by evaporation. Preferably, evaporation is carried out under reduced pressure (40-150 mbar). Organic acids (acid acetic, butyric acid, lactic acid) can also be partially eliminated during this evaporation process.

In a specific embodiment of the invention, the purification method comprises a step of bleaching after adding glycerol. "Bleaching" means evaporating a 50%, 60%, 70%, 80%, 90% to 99% fraction of the mixture. The objective is to maintain the heavy products and salts at the bottom and to work on the pre-purified mixture recovered at the top.

The purification of alcohol from the aqueous solution can be carried out by distillation. Elimination by the distillation of products with a vapor pressure greater than that of the alcohol to be purified and products with a vapor pressure less than that of the alcohol to be purified is carried out according to conventional techniques known to persons skilled in the art. Preferably, the distillation steps take place at a pressure below 60 mbar. During topping, products with a vapor pressure greater than that of the alcohol to be purified are most notably water and organic acids. During stripping, products with a vapor pressure less than that of the alcohol to be purified are most notably glycerol and salts.

An optional step of the inventive purification method is adjusting pH to pH<7. Preferably, the pH of the aqueous solution is adjusted to pH<4, more preferentially to pH<3. This adjustment is achieved, for example, by adding $H_2SO_4$ or $HNO_3$. Preferably, sulfuric acid is used.

In one embodiment of the inventive method, purification of the alcohol comprises an extraction step using a hydrophobic solvent. Any suitable hydrophobic solvent can be used to purify the alcohol. Preferably, the hydrophobic solvent is selected among the following solvents: ethyl acetate, butyl acetate, methyl isobutyl ketone, n-butanol, toluene, benzene, n-hexane, isopentyl acetate, diisobutyl ketone, 5-nonanone, 2-ethyl-hexanal, 1-octanal, 2-methyl-hexanal, 1-heptanal, 3-heptanone, 2-nonanone, 2-octanone, 2-heptanone and n-heptyl acetate. Liquid-liquid extraction with a hydrophobic solvent makes it possible to extract the organic acids contained in the aqueous solution obtained after filtration or in the culture broth. In this case, subsequent elimination by distilling products with a vapor pressure greater than that of the alcohol leads primarily to eliminating water.

The step of extracting organic acids with a hydrophobic solvent can be carried out at various points of the inventive alcohol purification method.

Preferably, extracting with a hydrophobic solvent takes place after the step of adjusting the aqueous solution's pH. Indeed, acidification of the solution converts acetates into acids before extraction with the hydrophobic solvent.

In addition, persons skilled in the art will understand that the order of the steps of the inventive purification method can be modified. In particular, the order of the steps of eliminating water, adding glycerol, bleaching and adjusting pH can be modified. Thus, these operations can be performed in the following orders:

adjust pH, eliminate water, add glycerol;
adjust pH, add glycerol, eliminate water;
add glycerol, adjust pH, eliminate water.

In one embodiment of the invention, the method comprises a step of eliminating anions. Any suitable technique for eliminating anions can be used in the inventive methods. Eliminating anions using a strong anion-exchange resin can be cited in particular. Preferentially, this step is carried out before or after the water elimination step.

In an advantageous embodiment of the inventive method, after recovering the alcohol, glycerol is recovered. The glycerol can be regenerated and then recycled in the purification process or the fermentation process. The glycerol can be recovered according to any suitable method and then recycled in the purification method. Preferably, the glycerol is recovered by distillation. The glycerol can for example be regenerated by short path distillation.

FIGURES

FIG. 1: Method for purifying 1,3-propanediol by adding glycerol.
(1) Microfiltration, (2) Ultrafiltration, (3) Nanofiltration, (4) Water evaporation, (5) Glycerol addition, (6) Topping, (7) Stripping.

Figure 2:
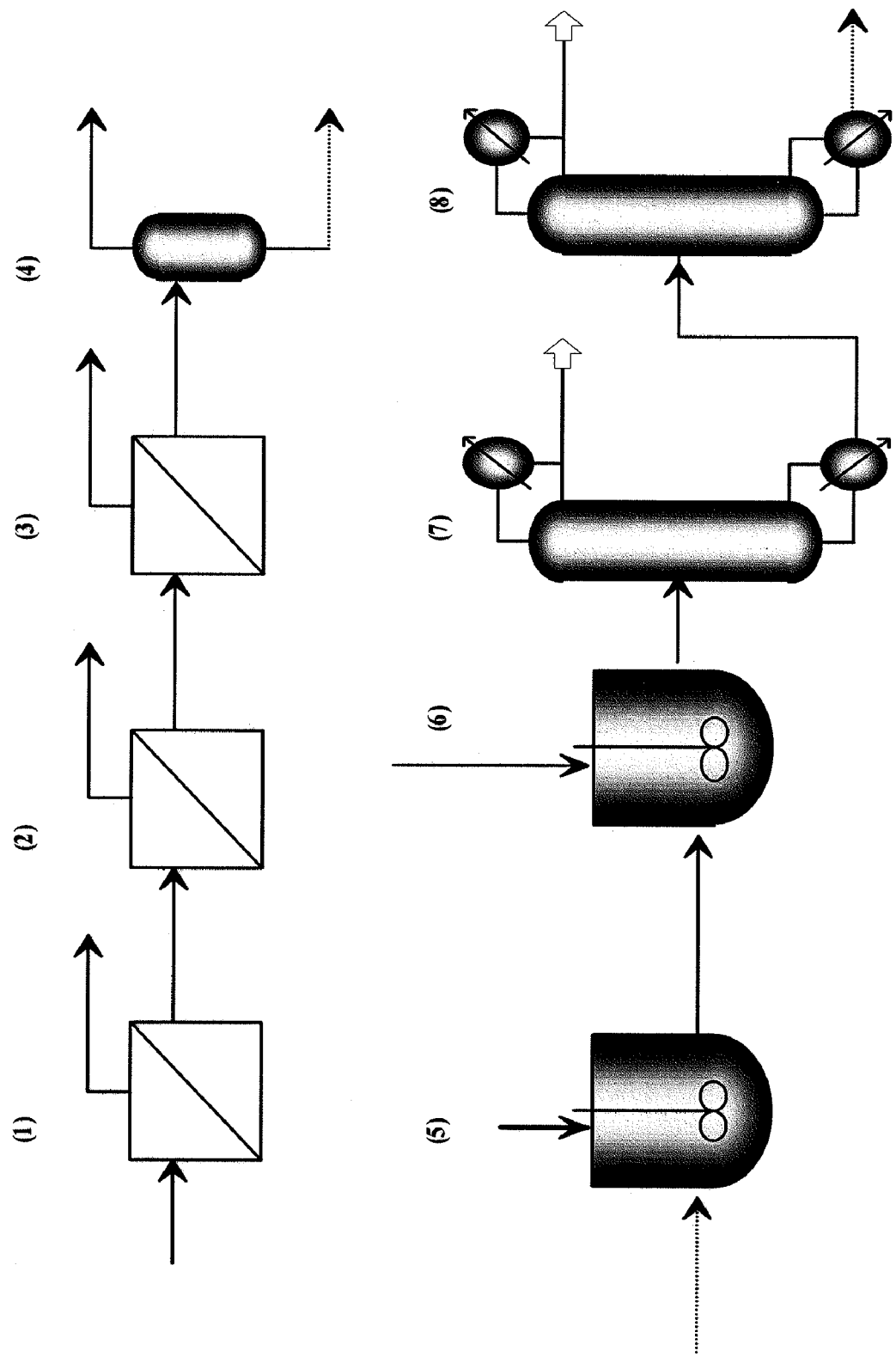

FIG. 2: Method for purifying organic acids and 1,3-propanediol by distillation, after acidification of the medium, and adding glycerol.
(1) Microfiltration, (2) Ultrafiltration, (3) Nanofiltration, (4) Water evaporation, (5) Acid addition, (6) Glycerol addition, (7) Topping, (8) Stripping.

Figure 3:
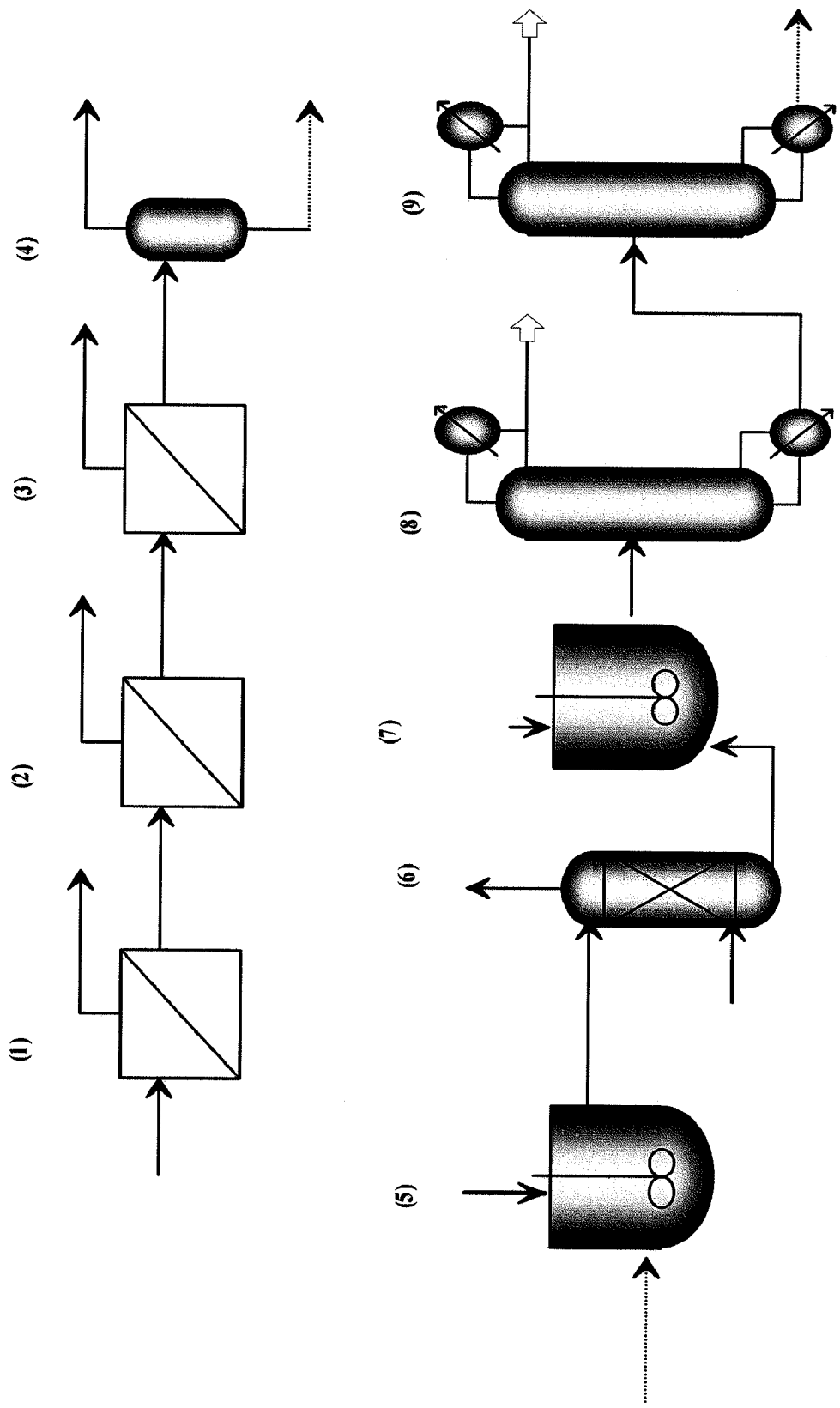

FIG. 3: Method for purifying organic acids by liquid-liquid extraction and 1,3-propanediol by distillation, after acidification of the medium and adding glycerol.
(1) Microfiltration, (2) Ultrafiltration, (3) Nanofiltration, (4) Water evaporation, (5) Acid addition, (6) Liquid-liquid extraction, (7) Glycerol addition, (8) Topping, (9) Stripping.

Figure 4:
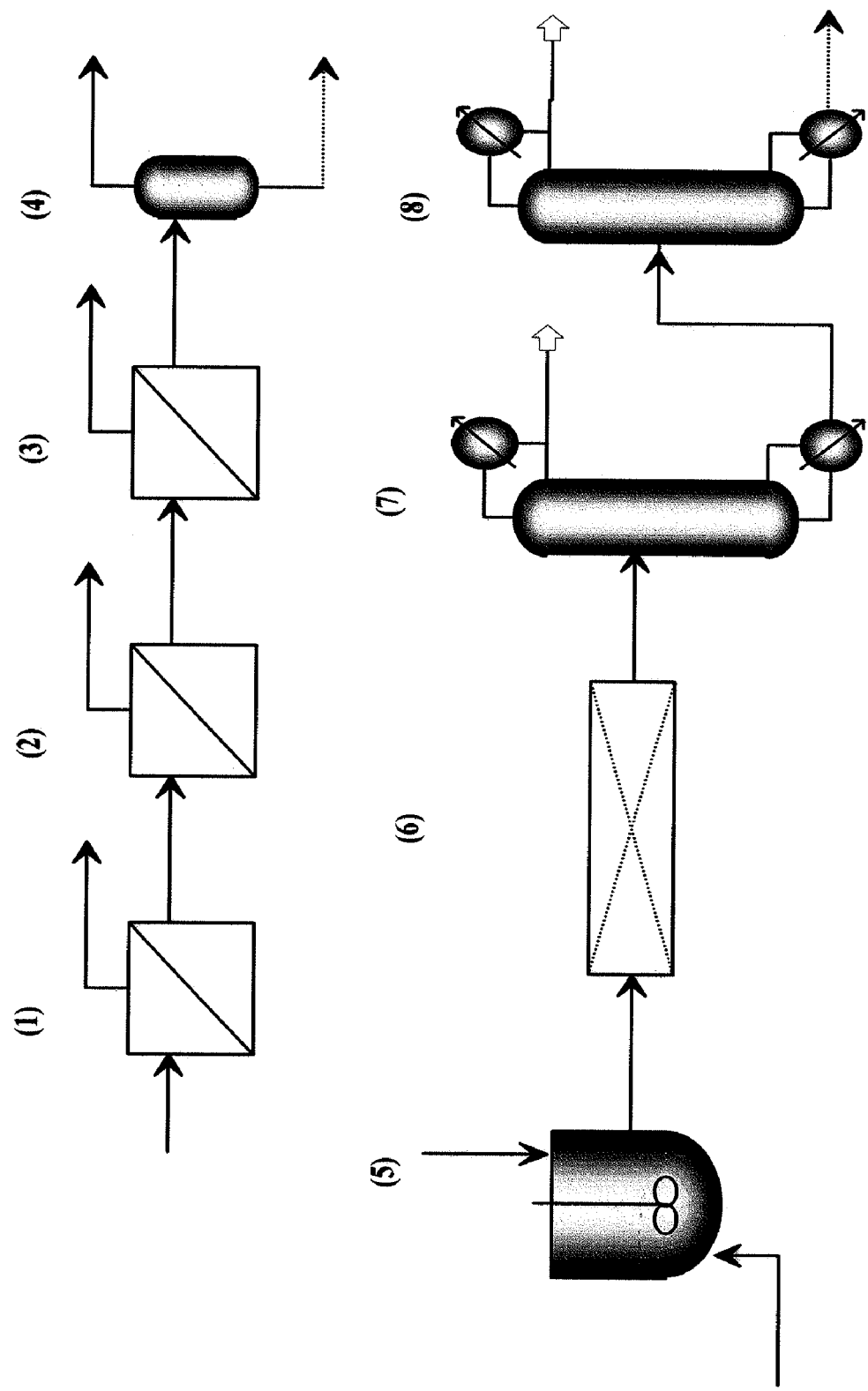

FIG. 4: Method for purifying 1,3-propanediol by distillation and elimination of anions by a strong anion-exchange resin, then adding glycerol optionally treated on an ion-exchange resin.
(1) Microfiltration, (2) Ultrafiltration, (3) Nanofiltration, (4) Water evaporation, (5) Glycerol addition, (6) Strong ion-exchange resin, (7) Topping, (8) Stripping.

Figure 5:
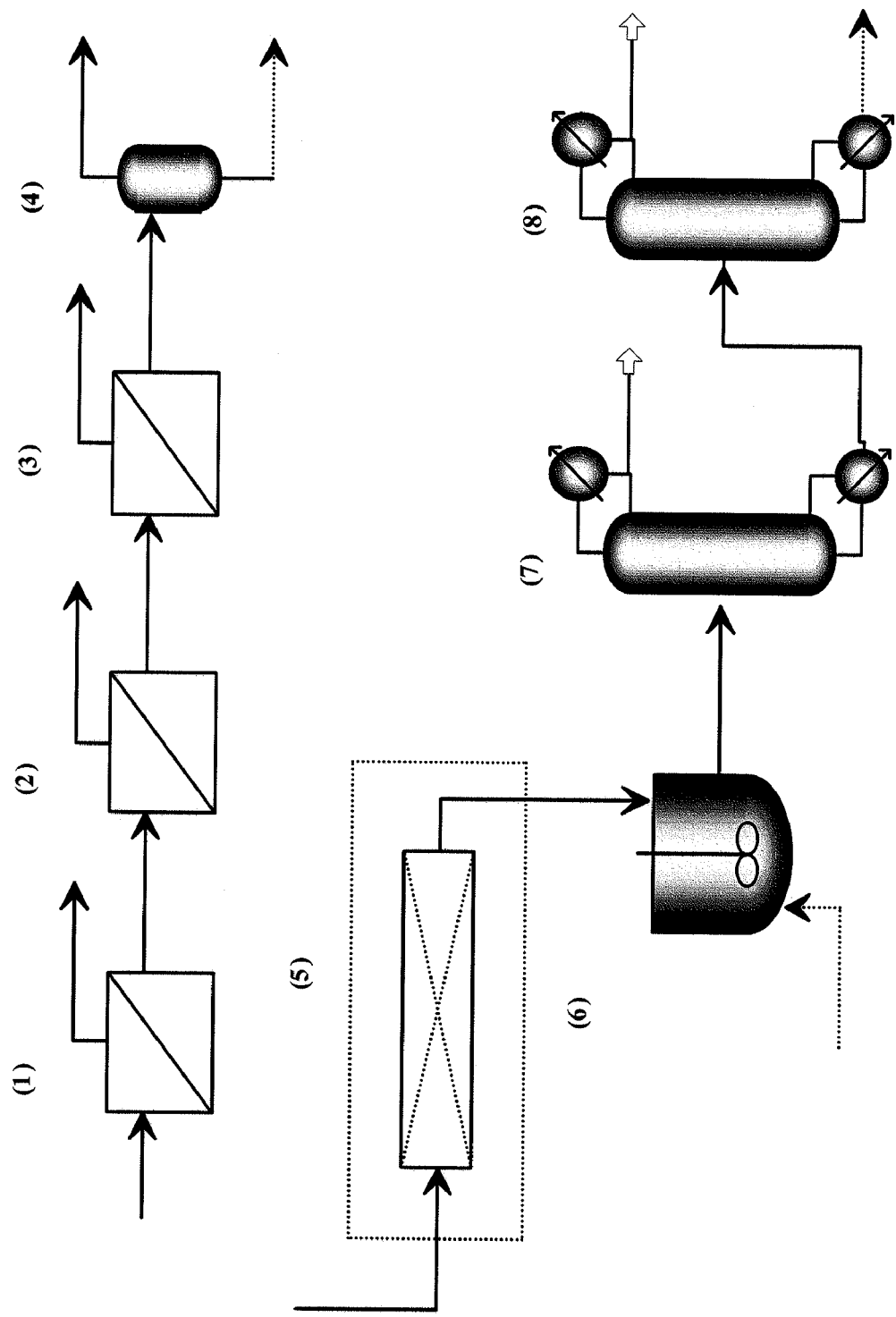

FIG. 5: Method for purifying 1,3-propanediol by distillation after adding glycerol optionally treated on an ion-exchange resin.
(1) Microfiltration, (2) Ultrafiltration, (3) Nanofiltration, (4) Water evaporation, (5) Treatment of glycerol on an ion-exchange resin, (6) Glycerol addition, (7) Topping, (8) Stripping.

Figure 6:
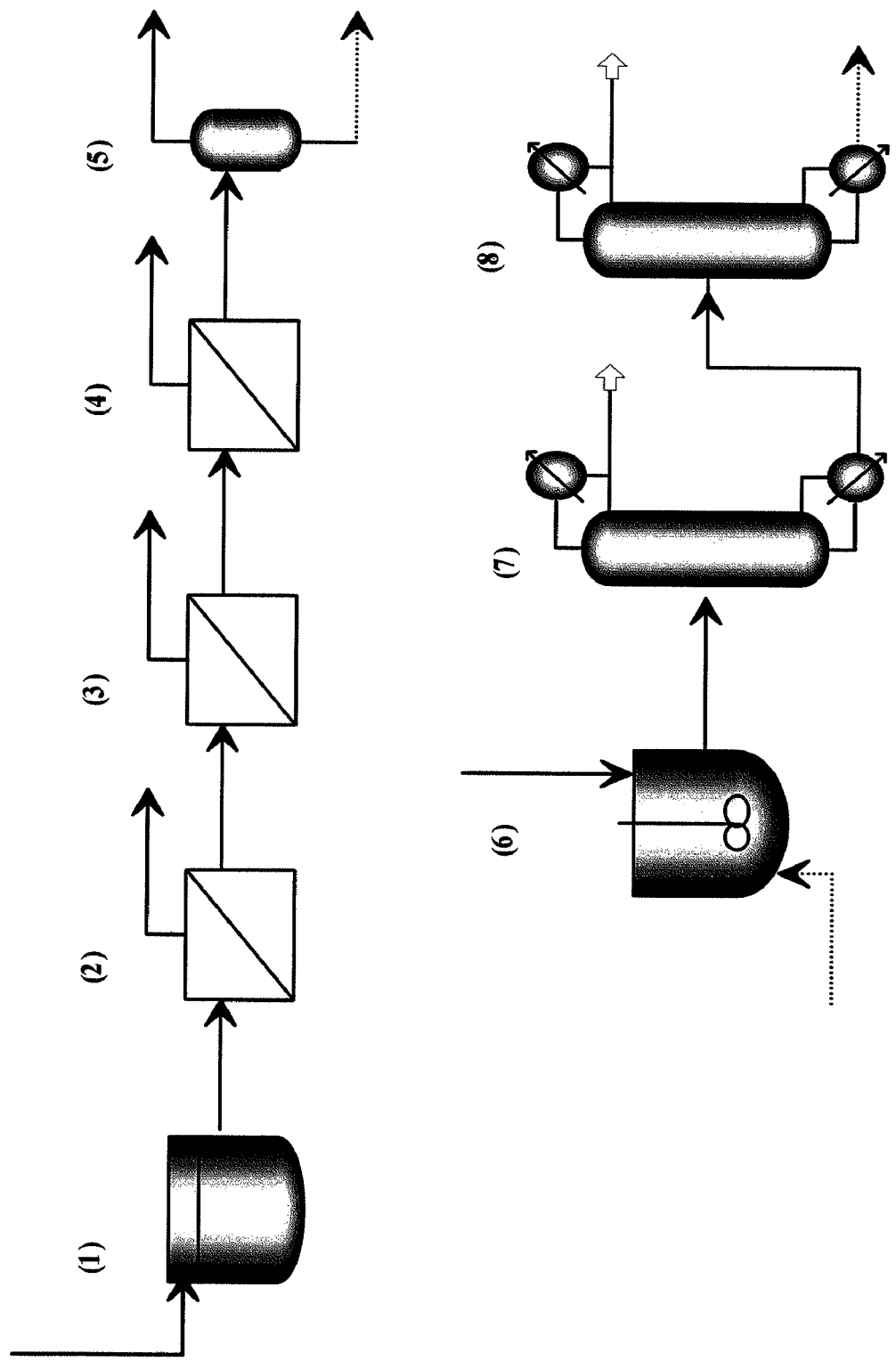

FIG. 6: Method for quenching fermentation by adding a base and purifying 1,3-propanediol by distillation after adding glycerol optionally treated on an ion-exchange resin.
(1) Quenching fermentation by adding a base, (2) Microfiltration, (3) Ultrafiltration, (4) Nanofiltration, (5) Water evaporation, (6) Glycerol addition, (7) Topping, (8) Stripping.

Figure 7:
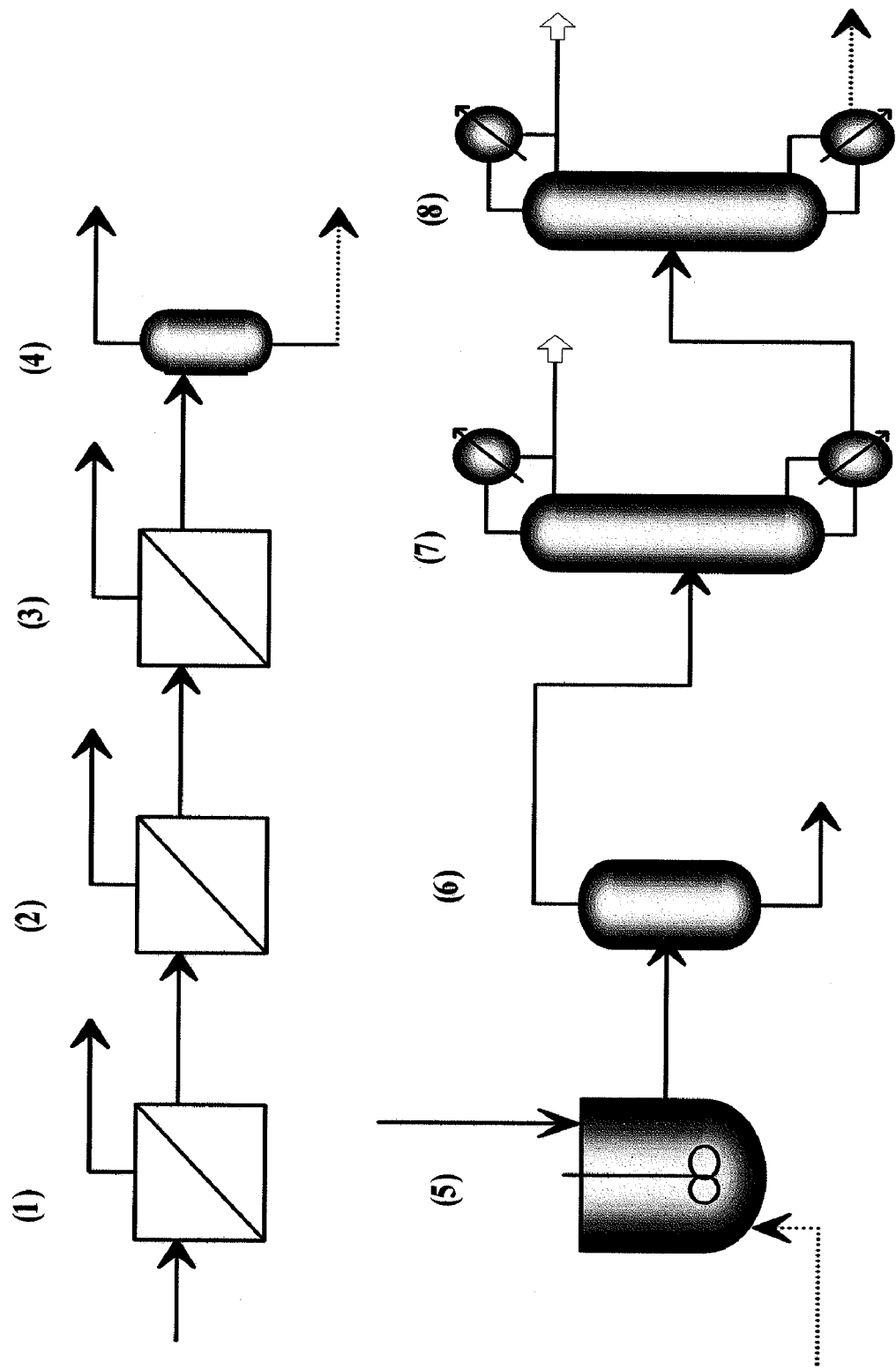

FIG. 7: Method for purifying 1,3-propanediol by adding glycerol and bleaching of the fermentation must.
(1) Microfiltration, (2) Ultrafiltration, (3) Nanofiltration, (4) Water evaporation, (5) Glycerol addition, (6) Bleaching (evaporation), (7) Topping, (8) Stripping.

EXAMPLES

Example 1

Example 1 relates to the basic invention:

100 ml of fermentation broth containing water, 1,3-propanediol, acid acetic, butyric acid, mineral salts and organic salts (ammonium, sodium acetate) are filtered by microfiltration, ultrafiltration and nanofiltration.

The resulting mixture is heated under 30 mbar to evaporate water.

Glycerol is added to the medium.

The resulting mixture is distilled on a 20-theoretical-stage column under 5 mbar of pressure. Volatile products are eliminated (primarily water and acid acetic).

The resulting mixture is distilled on a 20-theoretical-stage column under 1 mbar of pressure.

The 1,3-propanediol obtained is greater than 99% pure. Chlorides are undetectable.

Example 2

100 ml of fermentation broth containing water, 1,3-propanediol, acid acetic, butyric acid, mineral salts and organic salts (ammonium, sodium acetate) are filtered by microfiltration, ultrafiltration and nanofiltration.

The resulting mixture is heated under 30 mbar to evaporate the water.

50 g of glycerol are passed through a strong anion-exchange resin to eliminate anions, primarily chlorides. Glycerol is added to the fermentation mixture.

The resulting mixture is distilled on a 20-theoretical-stage column under 5 mbar of pressure. Volatile products are eliminated (primarily water and acid acetic).

The resulting mixture is distilled on a 20-theoretical-stage column under 1 mbar of pressure.

The 1,3-propanediol obtained is greater than 99% pure. Chlorides are undetectable.

The invention claimed is:

1. A method for purifying an alcohol from a fermentation broth, comprising at least the following steps:
   filtering the fermentation broth in order to obtain an aqueous solution containing the alcohol,
   eliminating water from the aqueous solution,
   adding glycerol to the aqueous solution,
   eliminating by distillation products with a vapor pressure greater than that of the alcohol to be purified,
   eliminating by distillation products with a vapor pressure less than that of the alcohol to be purified,
   recovering the alcohol,
wherein the alcohol is 1,3-propanediol, 1,2-propanediol, or a mixture thereof, and wherein the addition of glycerol to the aqueous solution containing the alcohol solubilizes salts by retaining the salts in liquid phase until the end of the purification process.

2. A purification method according to claim 1, further comprising a step of adjusting the pH of the aqueous solution to pH<3.

3. A purification method according to claim 1, further comprising a step of extracting with a hydrophobic solvent to eliminate organic acids.

4. A purification method according to claim 1, further comprising a step of eliminating anions in the aqueous solution.

5. A method according to claim 1, wherein water is eliminated by evaporation.

6. A method according to claim 1, wherein glycerol is added in a proportion ranging from 5% to 100% by weight of the aqueous solution.

7. A method according to claim 1, wherein the alcohol to be purified from the culture broth is 1,3-propanediol.

8. A method according to claim 1, wherein after the alcohol has been recovered, glycerol is recovered.

9. A method according to claim 1, wherein the added glycerol is pre-treated with a strong anion-exchange resin to eliminate anions from the crude glycerol.

10. A method according to claim 1, further comprising a step of bleaching after adding glycerol.

* * * * *